US00PP27445P2

(12) United States Plant Patent
Stemkens

(10) Patent No.: US PP27,445 P2
(45) Date of Patent: Dec. 6, 2016

(54) ***GAILLARDIA* PLANT NAMED 'GAIZ0003'**

(50) Latin Name: ***Gaillardia aristata* Purch.**
Varietal Denomination: GAIZ0003

(71) Applicant: SYNGENTA PARTICIPATIONS AG, Basel (CH)

(72) Inventor: Henricus Godefridus Wilhelmus Stemkens, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 10 days.

(21) Appl. No.: 14/121,531

(22) Filed: Sep. 16, 2014

(51) Int. Cl.
*A01H 5/02* (2006.01)

(52) U.S. Cl.
USPC ..... Plt./431

(58) Field of Classification Search
USPC ..... Plt./431
See application file for complete search history.

(56) References Cited

PUBLICATIONS

Pluto Plant Variety Database Feb. 19, 2016, retrieved on Feb. 22, 2016, retireved from the Internet at <https://www3.wipo.int/pluto/user/en/index.jsp> 1 page.*

* cited by examiner

*Primary Examiner* — June Hwu
(74) *Attorney, Agent, or Firm* — Joshua L. Price

(57) ABSTRACT

A new *Gaillardia* plant named 'GAIZ0003' particularly distinguished by the medium two-toned yellow and yellow-orange inflorescences, held well above the foliage, medium-deep green foliage, medium sized and semi-upright plant habit with good branching.

1 Drawing Sheet

Latin name of the genus and species of the plant claimed: *Gaillardia aristata* Purch.

Varietal denomination: 'GAIZ0003'.

BACKGROUND OF THE NEW PLANT

The present invention comprises a *Gaillardia* plant, botanically known as *Gaillardia aristata*, and hereinafter referred to by the variety name 'GAIZ0003'.

'GAIZ0003' is a product of a planned breeding program. The new cultivar has medium sized, orange-eyed, two-toned, yellow-orange and yellow inflorescences held well above the foliage, medium to deep green foliage, medium sized and semi-upright plant habit with good branching.

'GAIZ0003' originated from an open pollination occurring in the summer of 2007 in a controlled environment in Enkhuizen, Netherlands. The female parent was an unpatented plant identified as 'K9204-22', having yellow inflorescences and a more mounding and less upright plant habit than 'GAIZ0003'.

The male parent is unknown, because this was an open pollination with a cloud of pollen from the whole population.

The resulting seeds were sown in Enkhuizen, Netherlands in March 2008. 'GAIZ0003' was selected as one flowering plant (designated 'L5587-1') within the progeny of the stated cross in July 2008.

The first act of asexual reproduction of 'GAIZ0003' was accomplished when stem cuttings were propagated from the initial selection in October 2008 in a controlled environment in Enkhuizen, Netherlands.

BRIEF SUMMARY OF THE INVENTION

Horticultural examination of plants grown from cuttings of the plant initiated in the spring of 2009 in Enkhuizen, Netherlands, and continuing thereafter, has demonstrated that the combination of characteristics as herein disclosed for 'GAIZ0003' are firmly fixed and are retained through successive generations of asexual reproduction.

'GAIZ0003' has not been observed under all possible environmental conditions. The phenotype may vary significantly with variations in environment such as temperature, light intensity, and day length.

A Plant Breeder's Right for this cultivar has been applied for with the European Community Plant Variety Office (CPVO) on Oct. 25, 2012, #2012/2348. 'GAIZ0003' has not been made publicly available more than one year prior to the filing of this application.

The following traits have been repeatedly observed and are determined to be basic characteristics of the new variety. The combination of these characteristics distinguishes this *Gaillardia* as a new and distinct variety.

BRIEF DESCRIPTION OF THE PHOTOGRAPHS

The accompanying photographic drawing shows typical flower and foliage characteristics of 'GAIZ0003' with colors being as true as possible with an illustration of this type.

Figure 1:
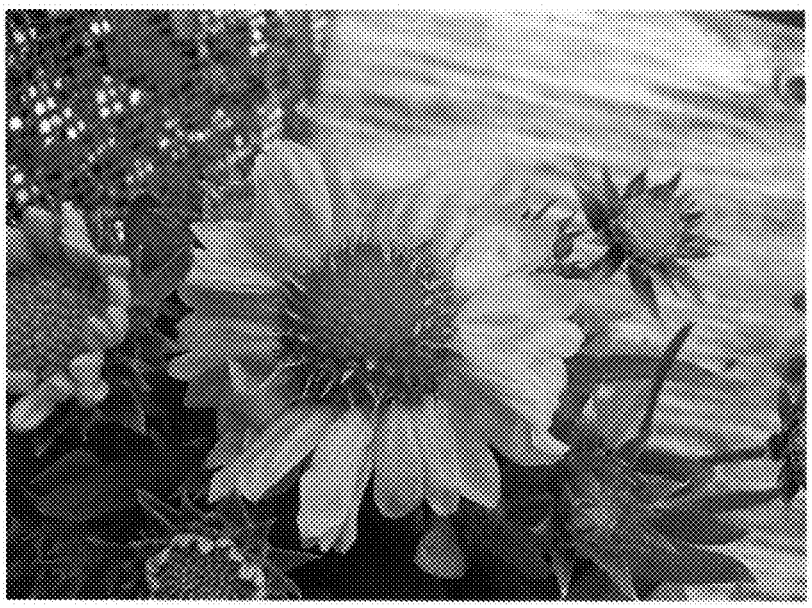
Figure 2:
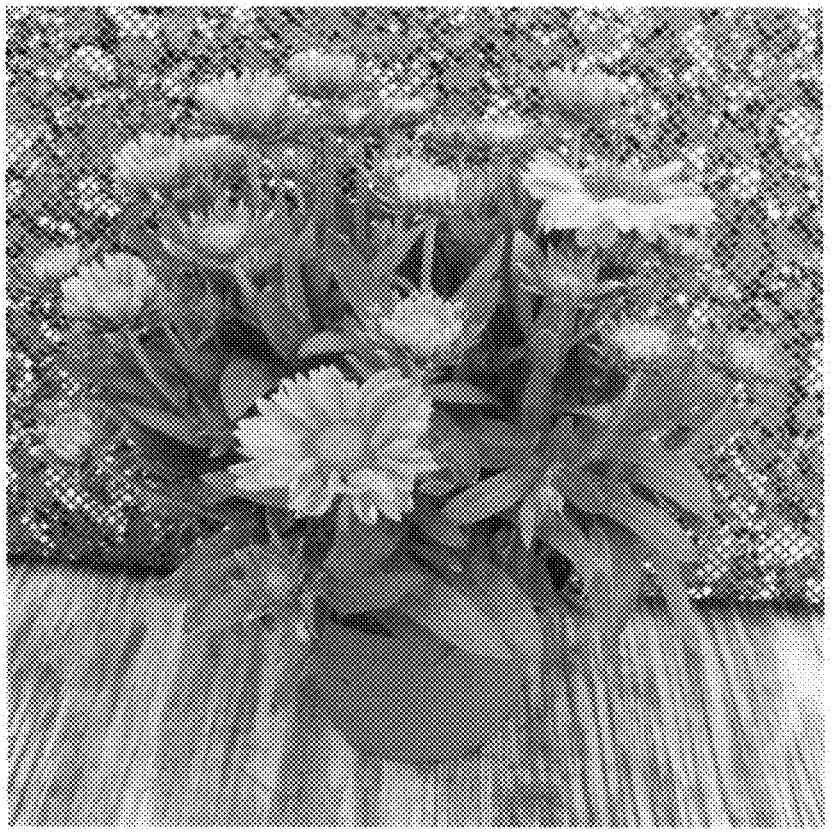

The photographic drawing shows in FIG. 1 a close-up of the inflorescence and in FIG. 2 a whole flowering plant of the new variety.

DETAILED BOTANICAL DESCRIPTION

The aforementioned photographs were taken on Apr. 28, 2013 from plants grown in a greenhouse trial in Andijk, Netherlands. These plants were grown in 12 cm pots and were approximately 3 months of age.

The plant descriptions and measurements were taken in Enkhuizen, Netherlands on Sep. 1, 2013 using 12-13 week old plants from an outdoor trial field. Cultivation of these plants had started in early June 2013 with planting rooted cuttings into 13 cm pots and growing them on the ground under natural outdoor conditions through the summer months.

Color references are made to The Royal Horticultural Society Colour Chart (R.H.S.) 2001

DIFFERENCES BETWEEN THE NEW VARIETY 'GAIZ0003' AND A SIMILAR VARIETY

TABLE 1

| | 'GAIZ0003' | 'GRANORAN' (U.S. Plant Pat. No. 19,749), also known as 'Sunrita Tangerine' |
|---|---|---|
| Start of flowering | One week later | One week earlier |
| Inflorescence diameter | 3.8-4.3 cm | 5.3 cm |
| Ray florets, aspect | Mainly flat, horizontal | At a later stage more drooping |
| Plant habit | More compact | More vigorous |

Plant:

*Type*.—Perennial, herbaceous, continuously flowering through the summer months, vernalization not essential for initiating of flowering, hardiness tolerates temperature above minus 10° centigrade temperature (frost).

*Form, growth and habit*.—Very tight and well-branched habit, relatively compact and small in size with the flower heads only a little above the foliage canopy.

*Plant height* (*without inflorescences*).—15.0-17.0 cm.

*Plant height* (*inflorescence included*).—21.0-27.0 cm.

*Plant width*.—23.0-25.0 cm.

Roots:

*Number of days to initiate and develop roots*.—21-25 days at about 22 degrees C.

*Type*.—Fine, fibrous, free branching.

*Color*.—RHS N155B but whiter.

Foliage:

*Arrangement*.—Alternate, simple leaves.

*Immature, leaf color, upper surface*.—RHS 138A.

*Lower surface*.—RHS 138B.

*Mature, leaf color, upper surface*.—RHS 138A.

*Lower surface*.—RHS 138B.

*Length*.—6.3-7.5 cm.

*Width*.—1.0-1.2 cm.

*Shape*.—Oblanceolate, upper leaves almost linear.

*Base shape*.—Attenuate.

*Apex shape*.—Acute.

*Margin*.—Mainly entire, margins of basal leaves are a little dentate at the tips.

*Texture, both surfaces*.—Very fine pubescence, single longer hairs along the margins and the midrib.

*Color of veins, upper surface*.—RHS 144A near base, for main part indistinct.

*Color of veins, lower surface*.—RHS 144A.

*Petiole color*.—Sessile, no petiole.

Stem:

*Quantity of main branches per plant*.—21-27, each with 1 to 4 secondary branches.

*Color of stem*.—From RHS 138B to RHS 138C.

*Stem length*.—About 13.0-18.0 cm.

*Stem diameter* (*at mid portion*).—0.3 cm.

*Length of internodes* (*at mid portion*).—1.5-2.0 cm mostly.

*Texture*.—Grooved, covered with hairs, medium density.

Peduncle:

*Color of peduncle*.—RHS 138B to RHS 138C.

*Length of peduncle*.—About 7.0-8.5 cm.

*Peduncle diameter*.—0.20-0.25 cm.

*Texture*.—Hairy, pubescent.

Inflorescence:

*Type*.—Capitulum (compositae-type), single inflorescences, borne terminally on short peduncles above the foliage.

*Quantity of inflorescences per plant*.—About 40 flower heads and buds.

*Lastingness of individual blooms on the plant*.—About two weeks depending on temperature.

*Fragrance*.—None.

Bud (just when opening/showing color):

*Color*.—About RHS 4A.

*Length*.—1 cm.

*Width*.—2.5-3.0 cm.

*Shape*.—Cup-shaped.

*Texture*.—Pubescent.

Young inflorescence:

*Diameter*.—About 3.2 cm.

*Color of rays, upper surface*.—Approximately RHS 3A, soon turning 12A.

*Color of rays, lower side*.—From RHS 4A to RHS 4B.

*Color of 'disc' with the disc florets still closed*.—Near RHS 151B.

Mature inflorescence:

*Shape*.—Medium sized, daisy-type inflorescences with two whorls of ray florets surrounding the disk, and more or less horizontally directed.

*Diameter of whole inflorescence*.—3.8-4.3 cm.

*Diameter of 'disc'*.—1.0-1.2 cm.

*Diameter of receptacle*.—About 1.5 cm (solid part, without the free lobes of the 'sepals').

Ray florets:

*Average quantity of ray florets*.—Two whorls, with 15-18 ray florets each.

*Color of floret, upper surface*.—RHS 25C in the middle portion, RHS 12A or RHS 13A near the tip and along the margins.

*Color of lower surface*.—RHS 11A.

*Length*.—1.7-1.9 cm.

*Width*.—1 cm.

*Shape*.—Ligulate to weakly oblanceolate.

*Apex shape*.—Tri-dentate, or else obtuse.

*Margin*.—Entire.

*Texture, upper surface*.—Glabrous.

*Texture, lower surface*.—Glabrous and mostly smooth, slightly protruding veins.

Disc florets:

*Average quantity of disc florets*.—About 40.

*Shape*.—Tube-shaped.

*Apex shape*.—5-pointed with acute tips.

*Color of young disk florets* (*just before opening*), *at apex*.—RHS 151B, light yellow-green.

*Color of open floret*.—RHS 34A, orange, at apex, fading towards base.
*Length of floret*.—0.5-0.7 cm.
*Width at apex*.—0.1-0.2 cm.

Involucre/receptacle:
*Shape*.—Flattened semi-sphere, formed by the phyllaries in an overlapping arrangement.
*Diameter* (*width*).—1.3 cm.
*Diameter* (*depth*).—0.6 cm.

Phyllaries:
*Quantity of phyllaries*.—16-20.
*Shape*.—Lanceolate.
*Apex shape*.—Acuminate.
*Base*.—Sessile, fused with receptacle.
*Margins*.—Entire.
*Color, outer surface*.—RHS 138A.
*Color, inner side*.—RHS 138B.
*Length*.—0.6 cm.
*Width*.—0.25-0.3 cm.
*Texture outer surface*.—Densely pubescent.
*Texture inner surface*.—Glabrous.

Reproductive organs:
*Gynoecium*.—Developed in disc and ray florets. Pistil, number per floret: One. Pistil, length: 1.2 cm. Style color: RHS 145D. Style length: 0.4 cm. Stigma color: RHS 143D. Stigma shape: Bi-lobed. Stigma, length: 0.4 cm. Ovary, length: 0.1 cm.
*Androecium*.—Present in disc florets only. Number of stamen: 4 per floret, tube. Filaments: Fused with the corolla tube. Anther, shape: Linear, 2 mm in length. Anther color: RHS 158D. Pollen amount: Plenty. Color of pollen: RHS 164A (brown-orange).
*Fertility/seed set*.—Flowers do not set seed, no seedset occurs and no fruit develops.
*Disease/pest resistance*.—Has not been observed on this hybrid.

What is claimed is:

1. A new and distinct variety of *Gaillardia* plant named 'GAIZ0003' substantially as illustrated and described herein.

* * * * *